United States Patent
Lang et al.

(10) Patent No.: US 7,725,658 B2
(45) Date of Patent: May 25, 2010

(54) SELF-OPTIMIZING CACHING SYSTEM AND METHOD FOR DATA RECORDS

(75) Inventors: Martin Lang, Höchstadt (DE); Ernst Bartsch, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 873 days.

(21) Appl. No.: 11/288,594

(22) Filed: Nov. 29, 2005

(65) Prior Publication Data

US 2007/0124541 A1 May 31, 2007

(51) Int. Cl.
*G06F 13/00* (2006.01)
*G06F 15/16* (2006.01)

(52) U.S. Cl. .................. 711/137; 711/135; 711/136; 711/147; 709/203; 709/217; 709/227; 709/232; 705/2; 600/300

(58) Field of Classification Search ......... 711/135–137, 711/147; 709/203, 217, 227, 232; 705/2; 707/10; 600/300
See application file for complete search history.

(56) References Cited

U.S. PATENT DOCUMENTS

| | | | | |
|---|---|---|---|---|
| 5,978,841 | A * | 11/1999 | Berger | 709/217 |
| 6,085,193 | A * | 7/2000 | Malkin et al. | 707/10 |
| 6,463,508 | B1 * | 10/2002 | Wolf et al. | 711/133 |
| 6,574,629 | B1 * | 6/2003 | Cooke et al. | 707/10 |
| 6,601,090 | B1 * | 7/2003 | Gurijala et al. | 709/213 |
| 6,721,780 | B1 * | 4/2004 | Kasriel et al. | 709/203 |
| 2002/0065931 | A1 * | 5/2002 | Goodwin et al. | 709/232 |
| 2003/0061451 | A1 * | 3/2003 | Beyda | 711/137 |
| 2004/0024812 | A1 * | 2/2004 | Park et al. | 709/203 |
| 2005/0096942 | A1 * | 5/2005 | Shachor | 705/2 |

OTHER PUBLICATIONS

Awerbuch et al, "Maintaining Database Consistency in Peer to Peer Networks", Technical Report CNDS-2002-2, http://www.cnds.jhu.edu, Feb. 6, 2002 (pp. 1-14).
BRIT Systems, Roentgen Files, http://www.brit.com/RoentgenFiles.htm, Sep. 7, 2005 (pp. 1-3).
"Rogan's 'Everything On-line' technology makes pre-fetching of digital medical images superfluous", Virtual Medical Worlds Monthy, http://www.hoise.com/vmw/00/articles/vmw/LV-VM-04-00-27.html, Jul. 27, 2005, (pp. 1-2).
A Density-Based Algorithm for Discovering Clusters in Large Spatial Databases with Noise—Martin Ester et al—Proceedings of 2nd International Conference on Knowledge Discovery and Data Mining (KDD-96) (1996).
Chameleon: A Hierarchical Clustering Algorithm Using Dynamic Modeling—George Karypis et al—IEEE Computer—1999.

* cited by examiner

*Primary Examiner*—Tuan V Thai
*Assistant Examiner*—Zhou H Li
(74) *Attorney, Agent, or Firm*—Schiff Hardin LLP

(57) ABSTRACT

A system and appertaining method provide for pre-fetching records from a central data base to a local storage area in order to reduce delays associated with the data transfers. User patterns for requesting data records are analyzed and rules/strategies are generated that permit an optimal pre-fetching of the records based on the user patterns. The rules/strategies are implemented by a routine that pre-fetches the data records so that users have the records available to them when needed.

17 Claims, 3 Drawing Sheets

SELF-OPTIMIZING CACHING SYSTEM AND METHOD FOR DATA RECORDS

BACKGROUND

In many fields, users must access and modify data located elsewhere on their own computers or workstations. In some situations, the volume of data needed by a user can be large and therefore it can be time consuming to download the needed information on demand. One example of such a situation is in the medical field where information about patients is stored in a central database. A patient typically undergoes various tests and examination procedures, such as x-ray, MRI, etc., and the results of these various procedures are stored in a common or distributed database. Medical personnel then access this information ("patient studies") for diagnostic and evaluative purposes.

Strategies have been devised by which users requiring such information can pre-fetch the patient studies prior to use so that the information is immediately available to them when needed.

Existing pre-fetching strategies currently follow fixed rules. For example, a typical rule is to pre-fetch all unread studies from the current day over the night so that by morning of the next day, all the studies reside at the users' workstation. The users do not have to load the studies from the previous day, because they were already pre-fetched at their workstation resulting in a loading time advantage.

This has been implemented in a number of ways. For example, as taught by Rogan in Rogan's "Everything Online" technology makes pre-fetching of digital medical images superfluous, http://www.hoise.cornlvmw/00/articles/vmw/LV-VM-04-00-27 html, Jun. 27, 2005 (herein incorporated by reference), a medical specialist presents a list of images which he wants to consult a day on beforehand in order to timely load them into the system. Overnight, the required images are then fetched in batch-mode out of a Picture Archiving and Communication System (PACS) to place them in stand-by locally. Proceeding in this manner was necessary since the available bandwidth often does not allow to directly download very large images. In most cases, local workstations have insufficient disk capacity to load a large number of large-sized image files.

However, the strategy proposed by Rogan is a static pre-fetching strategy, which does not take into account dynamic changes and the individual user behavior, as well as different individual hospital environments. Also this brute-force approach does not allow for fine tuned adjustments and/or for transferring only the relevant images in contrast to transferring the whole study.

Another approach is provided by BRIT Systems' Roentgen Files (see BRIT Systems Roentgen Files, http://www.brit.com/RoentgenFiles.htm, Jun. 27, 2005, herein incorporated by reference). In this system, pre-fetching is based on body-region, modality type and exam date. These downloaded exams can be pre-loaded to the viewer according to table driven rules. As with Rogan, pre-fetching is table driven or, in other words, static and not self-adapting and dynamic.

What is needed is an adaptive system that dynamically updates the pre-fetching strategy based on, e.g., an individual hospital environment and user behavior. Such an adaptive/dynamic system could result in a higher optimization potential than merely using static rules.

SUMMARY

The present invention relates to a self-optimization caching strategy for image data in which every workplace is not directly connected to the image data management, but rather is connected via a proxy service. All existing proxy services store their metadata (e.g., who accesses what data, where and when) in a centralized database, (the "metadata repository"). By using this information, one can mine for regularities of the data access and, using these, devise a pre-fetching strategy.

According to various embodiments of the invention, a pre-fetching cache service is provided that adapts automatically to the users' behavior and environment and a self-learning pre-fetching mechanism is provided that advantageously reduces image loading time after accessing a set of similar images on a regular basis.

All services, workstations and users that access/load image data from the image data management and/or other workstations can benefit from this inventive solution, which creates shorter perceived access/loading times for images, higher perceived loading performance of image viewing workstations, and self-optimizing workflow support, i.e., automated adaptation of the pre-fetching strategy to the customer/user needs and customer/user access behavior. Furthermore, the invention can help avoid peaks in network traffic and provide efficient image loading for high-volume reading, resulting in a more usable system.

DESCRIPTION OF THE DRAWINGS

An embodiment of the invention is described below with reference to the Figures discussed below.

DETAILED DESCRIPTION OF THE PREFERRED EMBODIMENTS

Figure 1:
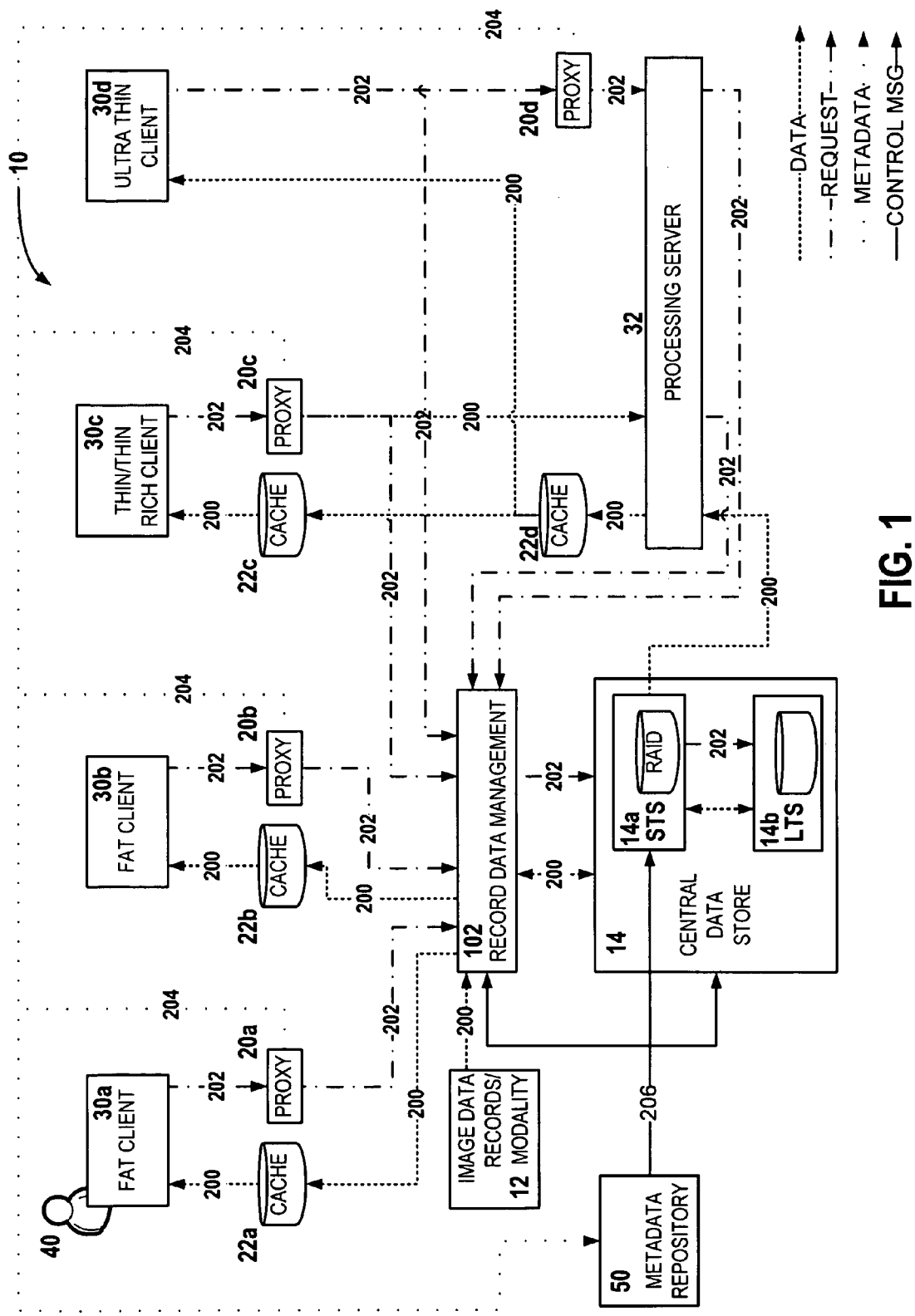
FIG. 1 is a block diagram illustrating the primary components of the system.

FIG. 1 illustrates an embodiment of the invention utilizing the pre-fetching of records. The embodiment described below relates to a medical institution setting where the data records comprise image data, however, the invention can be generalized to any type of database system.

Populating the Central Data Store

In an initial stage, the system 10 operates according to a traditional design. Data records related to a patient are gathered by an entity that serves as a record source 12. Such a record source 12 could be imaging devices, such as an x-ray machine, MRI, CAT scan, or other known imaging devices. In addition, the record source 12 could be any other type of computer-based system, such as a data entry terminal or the like. In FIG. 1, the record source 12 is reflected in image data records related to a modality of the images. According to this embodiment, patient-related data records 200 are stored in a central data store 14 after passing through a record data management function 102. These data records 200 can include records of any type, but according to an embodiment of the invention relate to image data of various modalities, such as CT, MR, etc.

Central data store 14 could be a implemented as a physically centralized database or could be constructed as a distributed data base; in either case, the central data store 14 serves as a place where patent records are aggregated. The records may contain information such as a patient ID, an identifier for the type of data represented in the record, the medical personnel associated with the record, a ward or location identifier, etc. This central data store 14 could be implemented as part of the previously mentioned PACS system in a clinical environment.

Furthermore, the central data store 14 may be broken down into a short-term data store STS 14a and a long-term data store LTS 14b. The STS 14a could be implemented by a random access memory (RAM), cache, hard drive (that could include a RAID storage system), local file system, local data base, that is easily and immediately available to provide data to a requestor. The LTS 14b could be implemented by any form of a data archival system and could include CD/DVD jukebox, tape archive, or any form of archival storage. The LTS 14b utilizes a storage that is relatively inexpensive for storing large volumes of data and is able to maintain the data for long periods of time without degradation—however, the LTS 14b may require user intervention, such as the loading of tapes or disks, or may be considerably slower in providing data when requested, possibly due to the use of carousels or the like in retrieving the physical media upon which the data is stored or possibly due to the inherent slowness in data transfer of the media reading mechanism. When the LTS 14b is utilized for storage, the prefetch/preload mechanism can be used to load data to the STS 14b.

Querying the Central Data Store and the Proxy Server/Service

A user 40 wishing to access a patient's data record 200 is logged into a workstation client 30a-30d that accesses application permitting the user 40 to view or modify image data or other data records 200 obtained via a query or request 202. The workstation clients 30a-30d may be classified according to the functionality they are capable of performing. The workstation clients may be fat clients 30a, 30b, thin or thin-rich clients 30c, or ultra-thin clients 30d.

A central processing server 32 may be used in conjunction with the workstation clients 30c, 30d, depending on their capability. A processing server 32 is a server that calculates the display content from the image data from the image data management 102 and sends only the display data to one or more thin clients 30c, 30d. In the case of 3D image data, the processing server 32 calculates the 3D volume and would only send the desired 2D images to the thin client 30c, 30d, but not the whole 3D volume. In case when a central processing server 32 is used, the prefetch/preload mechanism is used to load data 200 to the processing server 32 and not to the physical local workplace 30c, 30d of the user 40. The processing server 32 supports these clients 30c, 30d by performing heavy processing jobs, such as the conversion of 3-D data into 2-D display representations noted above.

However, the central processing server 32 is not needed when the workstation client 30a, 30b is capable of performing its own heavy processing. The following list identifies some workstation client 30 possibilities:

| | |
|---|---|
| fat client 30a, 30b | processes all jobs, including graphical user interface (GUI) and advanced graphics processing without the help of the processing server 32 |
| thin-rich client 30c | the GUI and some basic graphic processing runs on the client 30c, with more advanced graphics processing being run on the processing server 32 |
| thin client 30c | the GUI runs on the client 30c, but the graphics processing runs on the processing server 32 |
| ultra-thin client 30d | the majority of processing, even the GUI, runs on the processing server 32 |

When the user 40 makes a request for data records 202 from a one of the workstations 30a-30d, this request may be made by the user 40 selecting a data record from a work list presented on a monitor of the workstation 30a-30d. In certain situations, such as the ultra-thin client 30d situation, the request 202 may be sent in parallel to the proxy server 20d and to the record data management module 102. Alternately, the request 202 may be sent in series, first to the proxy server 20a-20c and then to the record data management module 102.

The proxy server 20a-20d extracts the metadata 204 of the query (e.g., the requesting user ID, the location originating the request 202 the workstation 30a-30d originating the request 202, the time of the request 202, any query restrictions, patient name, and possibly any other information related to the request 202, etc.) from the request 202 and stores this information (the metadata 204 of the query) in the local cache 22a-22d (note that a cache 22d and proxy server 20d may be associated with the processing server 32 as well). The requested data records 200 (e.g., images) are either retrieved from the central data store 14 by the proxy service 20a-20d or by the record data management module 102 depending whether the requested records 200 are either locally cached 22a-22d in the proxy service 20a-20d, or not. The local cache, i.e., local record/data store 22a-22d, can be a random access memory (RAM), cache, hard drive, local file system, local data base, etc. on either a client or another server (i.e., processing server 32).

The requested data record 200 is copied to a local storage area cache 22a-22d of the workstation 30a-30d where the user 40 can access it for evaluation and possibly make modifications.

Collecting the Metadata from the Proxy Servers

In contrast to the known accessing systems, however, metadata 204 from the data record requests 202 is additionally provided by the proxy servers 20a-20d, based on the request for data records 202, to a metadata repository 50 (FIG. 2) that stores the metadata in a raw metadata storage area/cache 52, which can include the similarities of query results (e.g., the attribute ward is equal, the date is today, etc.). The metadata repository 50 collects metadata 204 from all proxy servers 20a-20d in the system and aggregates all of the metadata 204 into the raw metadata storage area 52. The metadata can be pushed into the metadata storage area 52 by the proxy servers 20a-20d, or it may be pulled into the metadata storage area 52 from the proxy servers 20a-20d, and this can be implemented as an asynchronous (e.g., interrupt) or synchronous (e.g., polled) mechanism.

It is also possible that the metadata repository 50 contains a cache (possibly RAM, a file system, or other known caching mechanisms) to store the requested data records 200 to relieve the burden on the central data store from providing multiple copies of the same data record 200. This cache may alternately be associated with the record data management module 102.

Translating Aggregated Metadata into Rules and Strategies

Figure 2:
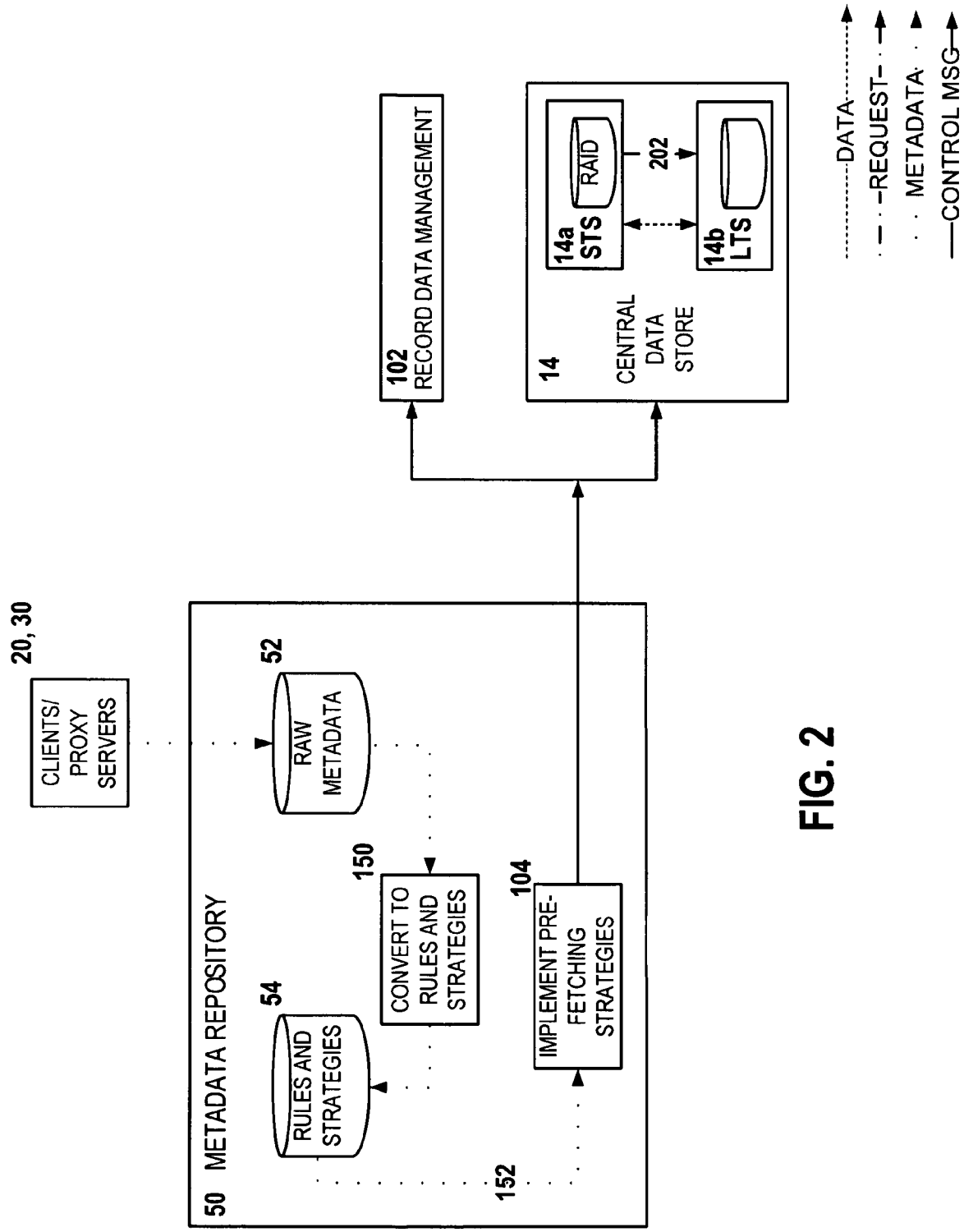
FIG. 2 is a block diagram showing an expanded portion of the metadata repository.

As illustrated in FIG. 2, the metadata repository 50 contains or has associated with it a conversion routine 150 that takes the aggregated raw metadata from the data store 52 and converts this into rules and strategies that are stored in a rules and strategies database 54. The conversion routine 150 mines the metadata 204 and determines regularities based on information contained within the metadata.

Figure 3:
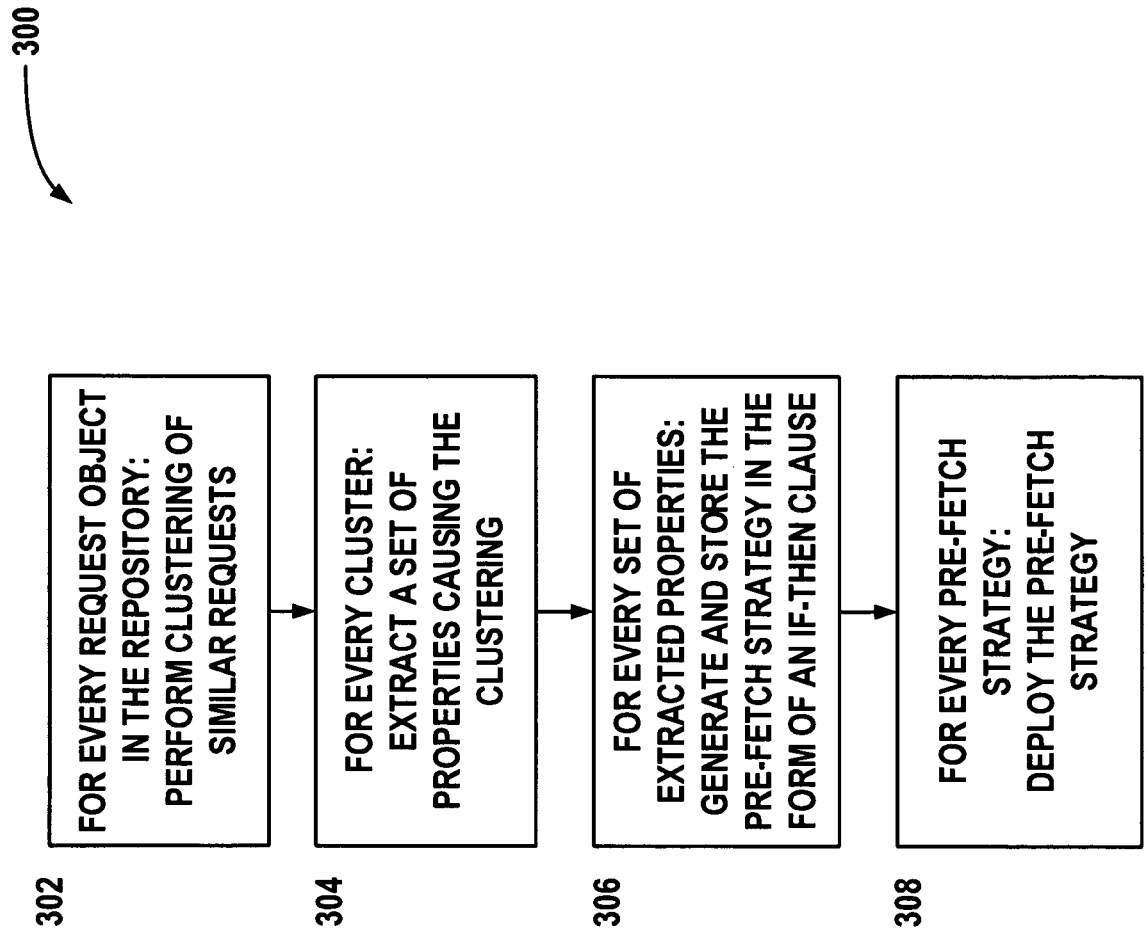
FIG. 3 is a flow chart illustrating the conversion to rules and strategies and deployment of the pre-fetch strategies.

FIG. 3 illustrates the process 300 for converting the aggregated raw metadata into rules and pre-fetch strategies. Accordingly, in a first step 302, for ever request object in the repository, a clustering of similar requests is performed. Theoretically, both density-based, hierarchical and partitioning (flat) clustering algorithms can be used to mine for regularities in the raw metadata, to find groups of requests which have strong similarities or address similar documents or datasets. Therefore each request is represented as an object in the raw metadata database 52. In a preferred embodiment, every request object has a vector of k properties, describing the characteristics of the request, such as the requesting user 40, its role, the workstation 30a-30d where the request was placed, the query statement itself, the time and weekday, etc. Based on this vector, the request objects can be set into relation to each other and a "distance" between two request objects can be computed for quantification of the similarity, using known vector-based mathematics.

Finding similarities and regularities in a set of recorded requests is then done by grouping similar, close-by objects into clusters. Therefore, both the density based partitioning algorithms, as well as the hybrid clustering approaches (which use a combination e.g., of the above mentioned approaches) has proven to be most promising and suitable.

Density based algorithms utilize growing clusters, which get extended as long as the density of objects in their neighborhood exceeds a predefined threshold. An example algorithm for the density based approach is the well-known DBSCAN-algorithm (Ester M., Kriegel H.-P., Sander J., Xu X.: A Density-Based Algorithm for Discovering Clusters in Large Spatial Databases with Noise, Proc. 2nd int. Conf. on Knowledge Discovery and Data Mining, Portland, Oregon, 1996, AAAI Press, 1996, herein incorporated by reference).

The hierarchical clustering algorithms stepwise aggregate objects into groups (agglomerative approach) or stepwise split/subdivide bigger groups into subgroups (divisive approach). Partitioning clustering methods assign the objects to a predefined number of clusters. The CHAMELEON algorithm can be mentioned as a suitable example for a hybrid clustering approach, using a combination of partitioning and hierarchical proceeding (G. Karypis, E-H Han, and V. Kumar. CHAMELEON: A hierarchical clustering algorithm using dynamic modeling. IEEE Computer, 32(8):68-75, 1999, herein incorporated by reference).

A second step 304 is performed to extract the cluster properties. For each previously identified cluster, the characteristic cluster properties are extracted. Based on the set of resulting clusters, which were retrieved by the, e.g., periodically run clustering algorithm, the cluster properties are extracted. Therefore, every cluster of related requests is examined for which properties of the requests had caused the clustering and therefore had an impact on the similarity of these requests. By way of example, a set of cluster properties for a specific cluster could be that all requests address mainly x-ray images, which acquision date is equal to the date of the query/request and were requested/posted by a user named "John Smith" and mainly from a workstation labeled "WS1264".

The third step 306 is to derive/generate the pre-fetch strategies from the cluster properties. Using the previous example, this would translate into the following strategy "always pre-fetch/mirror images from the x-ray ward identifying John Smith as a user and send them to workstation WS1264."

The fourth and final step 308 is to implement the derived/generated strategy by sending the appropriate control messages to (102, 14, 14a, 14b) or triggering the appropriate sub-systems (102, 14, 14a, 14b). All of the rules and strategies so developed are stored in the rules and strategies database 54.

Implementing the Pre-Fetch Strategies

The rules and strategies developed as described above must then be implemented. An implement pre-fetch strategies module 104 takes the strategies from the rules and strategies database 54 and begins making control requests 206 from the record data management module 102 based on these strategies 54. These requests 206 initiate the downloading of the data records 200 just the same as if the user 40 had actually made the requests 202 from the workstation 30a-30d itself. The implement pre-fetch strategies module 104 may incorporate various constraints that are not a part of the metadata itself, but rather constitute additional system factors to be considered.

For example, it may note that there is ample bandwidth available for downloading between the hours of 12am and 5am and therefore concentrate the downloading between these hours. Alternately, it may detect that the central data store 14 is experiencing an abnormal load at a particular time despite the fact that this time occurs during a time period of high available bandwidth. Therefore, it may decide to defer the requests for data records. Additional system factors could include that a particular user 40 will be on vacation for two weeks, or that one user should be substituted for another for a given period of time.

Thus, with this system, it is possible, for example, to detect regularities like: "User <A> always accesses the image data from <a certain modality> during <11am> to <1pm> at workplace <X>, <Y> or <Z>". By using this knowledge, the record data can be easily be pre-fetched at the corresponding proxy service. This technique results in shorter access/loading times for the image data sets.

It is important that data consistency at all caches and databases has to be ensured. This can be done by using one of the many available known replication and synchronization algorithms and strategies for distributed datasets (see, e.g., Baruch Awerbuch, Ciprian Tutu, "Maintaining Database Consistency in Peer to Peer Networks" (2002), http://citeseer.ist.psu.edu/503365.html, Jun. 27, 2005, herein incorporated by reference).

Exemplary Case Studies

The above discussed system can be explained with reference to the following hypothetical case study.

Dr. Smith always reads his CT and MR exams from 11am to 3pm at one of the three reading workstation of Radiology Department A. This trend is detected and the system automatically pre-fetches unread studies for Dr. Smith at these three reading workstations.

When Dr. Smith logs in at 11am on his workstation, the images are already loaded on these three workstations and he can immediately start her image reading. In the afternoon (after 3pm) however, Dr. Smith reads at a different radiology department, Radiology Department B. The system knows this by analyzing Dr. Smith's reading behavior (based on the metadata related to past requests of Dr. Smith) and pre-fetches the afternoon studies to Radiology Department B.

In contrast to Dr. Smith, Dr. Gonzales only reads at his reading workstation located in his office. Therefore, all of his studies are pre-fetched to only one workstation always.

A myriad of different possibilities of pre-fetching can be employed by this system. One is not restricted to only one pre-fetching rule, nor does the rule have to be static—it can change over time based on the monitored metadata relating to requests for data records.

The following table illustrates example rules 54 extracted from the metadata 52 by detecting the following trends:
  a) Usually Dr. Meier reads CT chest images at either Workstation A or B between 2pm and 5pm;
  b) Usually Dr. Muller reads MR images at Workstation C at no fixed time during the day.

TABLE

|  | User A: Dr. Meier | User B: Dr. Muller |
| --- | --- | --- |
| Workstation A | send last N unread CT chest studies to Workstation A |  |
| Workstation B | send last N unread CT chest studies to Workstation B |  |
| Workstation C |  | send last N unread MR studies to Workstation C |

Exemplary Strategies

In order not to overload the image data management with pre-fetching, a limited pre-fetching may be implemented by applying the following exemplary threshold mechanism. A threshold limit of, e.g., N=3 may be applied to always send only the last three unread studies. In this example, only the last three unread CT chest studies are sent to Workstation A and B and only the last three unread MR studies are send to Workstation C.

Dr. Meier selects the next unread CT chest study "Mrs. Schmidt" from the worklist at Workstation A. This study is already pre-fetched at the local cache of Workstation A and the study is loaded locally. Also, via a replication and synchronization mechanism such as that discussed above, Worksation B and the image data management are notified that Dr. Meier is currently reading the CT chest study from "Mrs. Schmidt". The CT chest study from "Mrs. Schmidt" is now reserved for Dr. Meier.

However, in case Dr. Meier wants to read an MR study at Workstation A, the corresponding study is not cached locally and has to be loaded from the record data management. In this case, Dr. Meier does not follow his usual pattern when reading images and hence the pre-fetching rule did not account for this behavior. In other words, when ever a user does not follow his/her regular reading pattern, the studies are not pre-fetched and have to be loaded from the image data management, which results in longer loading times. Nonetheless, repeated access from this new workstation is detected via the metadata each request generates, and the rules are adapted to accommodate new behavior by the users.

Any number of criteria may be used for establishing and defining the rules and strategies that are implemented by the system. Additionally, any type of information can be pre-fetched. The system is not limited to image data or even medical data.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, signal processing and/or control, data processing and the like.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

LIST OF REFERENCE CHARACTERS

| 10 | prefetch system |
| --- | --- |
| 12 | record source, modality of images |
| 14 | central data store |
| 14a | short term storage STS of the central data store |
| 14b | long term storage LTS of the central data store |
| 20a-20d | proxy servers |
| 22a-22d | local cache |
| 30a-30d | workstation clients: fat, thin/thin-rich, and ultra thin |
| 32 | processing server |
| 40 | user |
| 50 | metadata repository |
| 52 | metadata storage area |
| 54 | rules and strategies database |
| 102 | record data management |
| 150 | conversion routine |
| 200 | data records |
| 202 | query/request for records |
| 204 | metadata |
| 206 | control message |
| 300 | process for converting raw metadata into rules & strategies |
| 302-308 | method steps |

What is claimed is:

1. A method for pre-fetching data records from a central data store to a local data store, comprising the steps of:
   populating the central data store with records from a record source;
   making multiple requests by each of a plurality of respective users with each user having its own respective proxy service for downloading the records from the central data store to the local data store of the respective user by a record data management module via the respective proxy service so that the respective user is not directly connected to the record data management module, said respective proxy service outputting metadata defining who accesses what data, where, and when, and wherein each request has a request vector associated with it defining a plurality of characteristics of the request;

aggregating said metadata from all of said proxy services relating to all of said multiple requests from the respective users into a separate metadata repository which is separate from said users, central data store and said record data management module, and wherein said aggregating is initiated in an event driven manner by the proxy service in a poled manner by a routine associated with the metadata repository;

translating the metadata into dynamically created pre-fetch rules and strategies based on the respective user metadata and using the request vectors for quantification of relationships between requests, wherein similarities and regularities in requests are identified by grouping similar, close-by objects into clusters, using a density based algorithm for growing the clusters that are extended as long as a density of objects in a corresponding neighborhood exceeds a predefined threshold, and wherein the density based algorithm as well as a hybrid clustering which uses a combination of the request vector quantification and the density based algorithm is employed;

initiating by the record data management module automatic downloading of pre-fetched records from the central data store to the local data store of the respective user according to the pre-fetch rules and strategies; and updating the pre-fetch rules and strategies based on additional requests by the respective user for downloading the records from the central data store to the local data store.

2. The method according to claim 1, further comprising:
automatically downloading pre-fetched records to more than one local data store associated with the respective user according to the pre-fetch rules and strategies.

3. The method according to claim 1, further comprising:
sending the requests by the proxy service to the record data management module after receiving the requests.

4. The method according to claim 1, further comprising:
sending the requests to the proxy services and the record data management module in parallel.

5. The method according to claim 1, further comprising segregating, by the proxy services, the metadata from the request and locally storing this metadata.

6. The method according to claim 1, wherein the translating of the metadata into the pre-fetch rules and strategies further utilizes external information not contained within the metadata itself.

7. The method according to claim 6, wherein the external information is selected from the group consisting of central data store availability and utilization, network bandwidth, and user schedules.

8. The method according to claim 1, further comprising:
locally storing the records in a cache of the proxy service.

9. The method according to claim 1, further comprising:
caching the requested records in the metadata repository or the record data management module.

10. The method according to claim 9, wherein the metadata comprises a requesting user ID, a location originating the request, a workstation originating the request, and a time of the request.

11. The method according to claim 1, further comprising:
replicating and synchronizing the records for the purpose of error recovery.

12. The method according to claim 1, wherein the records comprise medical image data.

13. The method according to claim 12, wherein the record source is a medical imaging apparatus.

14. The method according to claim 1, wherein the central data store is implemented with a Picture Archiving and Communication System (PACS).

15. The method according to claim 1, wherein the local data store is selected from the group consisting of a random access memory, a hard drive, a local file system or a local database and is a local data store on a client or another server.

16. The method according to claim 1, wherein the translating of the metadata into the pre-fetch rules and strategies comprises:
creating said clusters of similar requests;
for every cluster, extracting a set of properties that caused the clustering; and
for every set of extracted properties, generating and storing the pre-fetch strategy.

17. The method according to claim 16, further comprising utilizing a hierarchical clustering algorithm that either: a) stepwise aggregates objects into groups in an agglomerative approach, or b) stepwise splits or subdivides bigger groups into subgroups in a partioning approach using said partioning algorithm.

* * * * *